United States Patent [19]
Berndt

[11] Patent Number: 5,310,658
[45] Date of Patent: May 10, 1994

[54] METHOD AND APPARATUS FOR DETECTING BIOLOGICAL ACTIVITIES IN A SPECIMEN

[75] Inventor: Klaus W. Berndt, Stewartstown, Pa.

[73] Assignee: Becton, Dickinson and Company, Franklin Lakes, N.J.

[21] Appl. No.: 959,192

[22] Filed: Oct. 9, 1992

[51] Int. Cl.$^5$ .......................... C12Q 1/06; C12M 1/34
[52] U.S. Cl. ......................................... 435/34; 422/79; 435/39; 435/291; 435/807; 435/808; 436/62; 436/148; 436/165
[58] Field of Search ................... 435/34, 39, 291, 807, 435/808; 436/62, 148, 165; 422/79, 106

[56] References Cited

U.S. PATENT DOCUMENTS

| | | | |
|---|---|---|---|
| 3,549,893 | 12/1970 | Gibbs | 356/338 X |
| 3,636,360 | 1/1972 | Oishi et al. | 356/136 X |
| 4,152,213 | 5/1979 | Ahnell | 435/34 |
| 4,220,715 | 9/1980 | Ahnell | 435/34 |
| 4,615,225 | 10/1986 | Sainz | 356/36 X |
| 4,926,681 | 5/1990 | Fitzpatrick | 73/52 |
| 4,945,060 | 7/1990 | Turner et al. | 435/291 |
| 4,952,498 | 8/1990 | Waters | 435/34 |
| 5,051,360 | 9/1991 | Waters | 435/34 |
| 5,094,955 | 3/1992 | Calandra et al. | 422/52 X |
| 5,155,019 | 10/1992 | Sussman et al. | 435/807 X |
| 5,232,839 | 8/1993 | Eden et al. | 435/34 X |

*Primary Examiner*—Robert J. Warden
*Assistant Examiner*—Robert Carpenter
*Attorney, Agent, or Firm*—Alan W. Fiedler

[57] ABSTRACT

A pressure/vacuum method and instrument for detecting biological activities in blood culture vials, that is non-invasive, does not require chemical sensors, does not require high-brightness short-wavelength light sources, is safe against eventual extreme high pressure values, and is head-space-temperature compensated. A culture medium and blood specimen are introduced into a sealable glass vial. The normally incompressible fluid suspension is made compressible through the use of a partially inflated gas bag submerged within the medium. The changes in fluid position that result from bacterial growth related pressure changes within the vial head space are measured to detect biological activities.

30 Claims, 11 Drawing Sheets

METHOD AND APPARATUS FOR DETECTING BIOLOGICAL ACTIVITIES IN A SPECIMEN

BACKGROUND OF THE INVENTION

The present invention relates to a non-invasive method and apparatus for detecting biological activities in a fluid specimen, such as blood. The specimen and a culture medium are introduced into a sealable container and exposed to conditions enabling metabolic processes to take place in the presence of microorganisms.

Usually, the presence of microorganisms such as bacteria in a patient's body fluids, particularly blood, is determined using blood culture vials. A small quantity of blood is injected through the sealing rubber septum into a sterile vial containing a culture medium. The vial is incubated at 37° C. and monitored for bacterial growth.

Common visual inspection involves monitoring the turbidity of the liquid suspension. Known instrumental methods detect changes in the carbon dioxide content in the head space of the culture bottles, which is a metabolic by-product of the bacterial growth. Monitoring the carbon dioxide content can be accomplished by methods well established in the art, including radiochemical, infrared absorption at a carbon dioxide spectral line, or pressure/vacuum measurement. These methods, however, require invasive procedures which result in the well-known problem of cross-contamination. In case of vacuum/pressure measurement, on the other hand, any temperature change within the vial head space also generates a pressure change which is not related to biological activities. Therefore, an additional head space temperature measurement is required in order to distinguish between biological and temperature effects. Non-invasive head space temperature monitoring, however, represents an extremely difficult problem, and there are currently no practical solutions. Further, the metabolic activity of some microorganisms can result in very high head space pressures. This means that while a pressure sensor has to be sensitive in order to allow detection of diverse microorganism species, it must also be protected from extreme pressure. Depending on the technology used, these two requirements often contradict each other and cannot be simultaneously satisfied.

Recently, novel non-invasive methods have been developed which use chemical sensors inside a vial. Such sensors often respond to changes in the carbon dioxide concentration by changing their color or by changing their fluorescence intensity. The outputs from these sensors are based upon light intensity measurements. This means that errors may occur, particularly if the light sources used to excite the sensors, or the photodetectors used to monitor intensities, exhibit aging effects over time.

The disadvantages of intensity-based methods can be overcome by utilizing modulated excitation light in combination with fluorescent sensors that change their decay time in response to changing carbon dioxide concentration. Using this method, intensity measurements are replaced with time measurements, so intensity changes do not influence the results. Current fluorescent decay time sensors, however, require high brightness short-wavelength light sources (550 nm or shorter) that are intensity-modulated at very high frequencies (typically above 100 MHz). A preferred embodiment would be a 5-mW green helium neon (HeNe) laser (543.5 nm), externally modulated by means of an acousto-optic light modulator. The laser/modulator combination is expensive, and it is expected that in practice the vials would have to be moved to the laser instead of having a light source for each vial. Further, such instruments would have moving parts and the time interval between successive measurements for each vial would be relatively long. And, it is not likely that inexpensive high-brightness short-wavelength semiconductor diode lasers will be developed in the near future.

SUMMARY OF THE INVENTION

The present invention overcomes problems identified in the prior art by providing a method and apparatus for detecting biological activities in blood culture bottles that is non-invasive, does not require chemical sensors or high-brightness short-wavelength light sources, is safe from extreme pressure, is head-space-temperature compensated, and is relatively inexpensive, such that each vial can be monitored continuously, meaning that diagnostic instruments may be constructed with non-moving vials.

According to the present invention, a culture medium and blood specimen are introduced into a sealable glass vial. The normally incompressible fluid suspension is made compressible, and the fluid level movement that results from microorganism growth related pressure changes within the vial head space may thus be measured.

A preferred method for making the fluid suspension compressible according to the present invention is to introduce a gas bag into the medium/blood mixture and submerge it below the upper level of the fluid, beneath the fluid-gas interface. It is also possible to introduce a plurality of small gas bags or compressible particles into the fluid, and then secure them. The contents of the gas bag may be atmospheric air, a mixture of gases, or other compressible fluids. As explained below, the pressure effect of head space temperature changes can be significantly reduced by using a gas bag filled with a gas having a density equal to that in the head space. In such a situation, an identical temperature change occurring within the head space and within the gas bag will result in identical pressure changes. Consequently, the fluid level will not be altered by a temperature change so that additional head space temperature monitoring is not required.

In order to monitor the fluid level inside the blood culture vial, an instrument according to the present invention has a light source arranged on one side of the vial, and a large-area photodetector on the other side of the vial. The light source and the photodetector are arranged so that if the fluid level changes, the percentage of the photodetector area receiving light from the lamp will also be affected, resulting in an altered photodetector output current. Thus, the head space pressure inside the blood culture vial can be monitored by recording the photodetector output signal.

In practice, the fluid-gas interface at an inner glass wall is shadow-imaged onto a large-area photodetector. It would be understood by someone skilled in the art that a lens system can also be used to realize the same imaging principle. An instrument according to the invention may include a color filter in the light path between the light source and the photodetector in order to increase the edge effect of the fluid-gas interface.

Gas bubbles are known to exist at the fluid-gas interface, particularly when the vials are shaken. Some forms of microorganisms also generate such gas bubbles. In order to circumvent problems connected with such bubbles, an instrument according to the invention may also include a sharp-edged opaque annular float disposed within the vial. When such a float is used, it is the upper float edge at an inner glass wall which is imaged onto the photodetector.

The pressure sensitivity of an instrument according to the present invention can be increased using an optical magnification effect. The distance between the light source and fluid or float edge can be made many times smaller than the distance between this edge and the photodetector.

A preferred light source would include a plurality of spaced horizontally oriented filaments. Such a light source allows the level monitoring system to be operated with varying amounts of blood inoculated into the vial.

An alternative embodiment of the present invention comprises a vial that is basically a glass tube with two flanges. A lower flange is sealed with a septum which has a gas bag secured to it. The gas bag can be attached to the septum before sealing the vial. The upper flange is used in the same manner as with ordinary vials, i.e., inoculation of the medium with blood.

In order to make the optical level monitoring system more accurate, the large-area analog photodetector can be split into two vertical segments. Both segments are covered with transmission masks containing grating-like horizontal elements. The grating-like elements of each segment are displaced relative to the elements of the other segment. Additionally, the two masks have a slightly different overall transmission. The two photodetector outputs are connected with the inputs of a differential amplifier. If the fluid level moves, the output signal of the amplifier shows oscillations in accordance with the mask grating constants, resulting in a trend over time concerning the output signal DC component. This trend establishes whether the fluid level is rising or falling, i.e., if the pressure is decreasing or increasing. In this way, the linearity of the level monitoring system is determined by the masks and can be made very high. It is also possible to use a linear photodetector array instead of the large area analog photodetector.

Besides a filament lamp, other acceptable light sources are those which have an extremely narrow emitting active area. These include light emitting diode chips and diode lasers. These latter light sources result in a very sharp edge imaging and, consequently, a high resolution.

According to another embodiment of the present invention, a culture medium and a blood specimen are introduced into a sealable glass vial. The vial is pivotally mounted. The normally incompressible fluid suspension is made compressible. Generally, at least one incompletely inflated gas bag is submerged below the upper level of the fluid on one side of the pivot point of the vial. Biological activities within the blood culture medium, such as bacterial growth processes, will result in a pressure change in the vial head space. This pressure change is transmitted through the fluid towards the gas within the gas bag which changes its volume. Due to the volume change of the gas bag gas, fluid moves from one side of the vial to the other, and the torque of the vial changes. Therefore, biological activities such as bacterial growth can be detected by monitoring the vial torque, e.g., through the use of a simple force sensor.

BRIEF DESCRIPTION OF THE DRAWINGS

The various features, objects, benefits, and advantages of the present invention will become more apparent upon reading the following detailed description of the preferred embodiments, along with the appended claims in conjunction with the drawings, wherein reference numerals identify corresponding components, and:

DETAILED DESCRIPTION OF THE PREFERRED EMBODIMENTS

Figure 1:
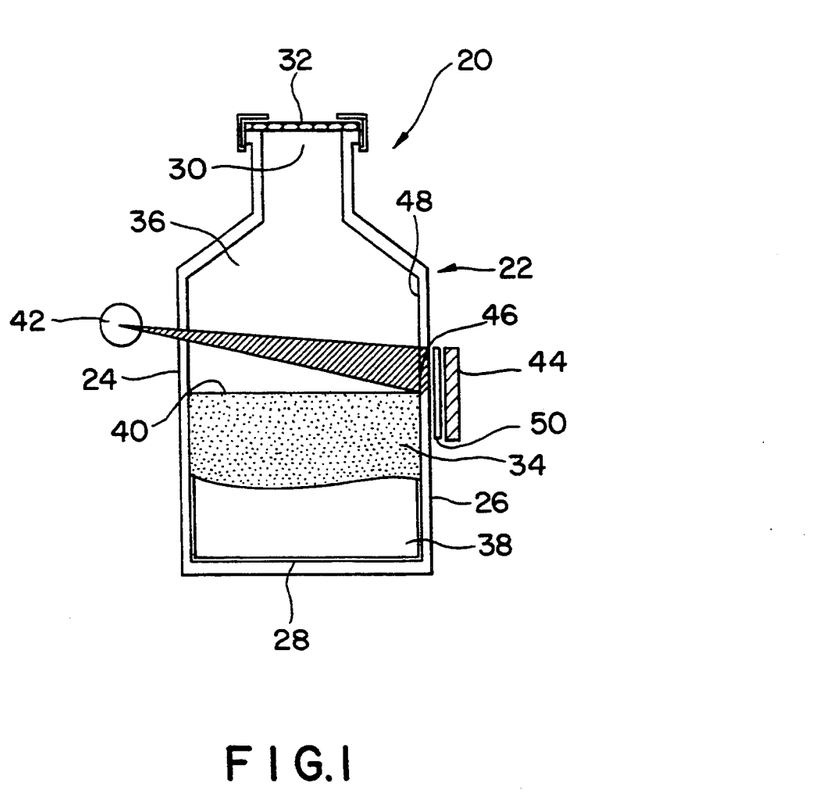
FIG. 1 shows an embodiment of the present invention in which the fluid-gas interface near the photodetector is imaged.

One embodiment of a detection instrument 20 embodying the principles and concepts of the present invention is depicted schematically in FIG. 1. The disclosed instrument comprises a glass vial 22 with two side walls 24 and 26, a bottom 28, and an opening 30 which is sealed with a septum 32. Vial 22 contains a combined medium/blood mixture 34 with a head space 36. The normally incompressible fluid is made compressible through the use of a gas bag 38 which is positioned below the upper level 40 of mixture 34, i.e., below the fluid-gas interface. While a gas bag is shown, it is also possible to introduce a plurality of small gas bags or compressible particles into the mixture, and then secure them, e.g., by means of a plastic mesh. In order to monitor the fluid level inside vial 22, a single filament light source 42 is arranged in close proximity to wall 24 and a large-area photodetector 44 is in close proximity to wall 26. Photodetector 44 may be a photodiode. Light source 42 and photodetector 44 are arranged so that an edge 46 of the fluid, the fluid-gas interface at the inner periphery 48 of wall 26, is shadow-imaged onto photodetector 44. If level of mixture 34 changes, the percentage of the photodetector area receiving light from the light source will also be affected, resulting in an altered photocurrent output signal. Thus, the pressure inside vial 22 can be monitored by recording the photodetector output signal. Other approaches, including a lens system, may be used as well.

Detection instrument 20 also includes a color filter 50 disposed between light source 42 and photodetector 44. It is used to increase the edge effect of the fluid-gas interface. Light source 42, photodetector 44, and filter 50 comprise the level monitoring system of detection instrument 20. It is well known that blood shows less absorption in the red spectral region than in the green/blue region. Therefore, filter 50 is a short-pass filter with a cutting wavelength of about 600 nm or shorter.

The function of gas bag 38 is explained in conjunction with the well-known equation:

$$pV = mRT \qquad (1)$$

In (1), the gas bag volume, V, the gas bag gas pressure, p, and the gas bag gas temperature, T, are interdependent parameters. The mass of gas enclosed in the gas bag is depicted by m while R is the universal gas constant. A bacterial growth-related pressure change within head space 36 will be transmitted toward gas bag 38, resulting in a volume change, dV, of the gas bag. For a constant temperature, the following pressure-related volume change may be derived from equation (1):

$$\frac{dV}{dp} = -\frac{V}{p}. \qquad (2)$$

If it is assumed that the gas bag has a cross-sectional area, A, identical to the inner vial cross-sectional area, and a height, h, a change of the gas bag volume V=Ah results in a change of the upper fluid level, dh, given by the following equation:

$$\frac{dh}{dp} = -\frac{h}{p}. \qquad (3)$$

In FIG. 1, air bag 38 does in fact have a cross-sectional area, A, identical to the inner cross-sectional area, A, of vial 22. Equation (3) shows that the pressure-related fluid level change, dh, is independent of the vial cross-sectional area, but is proportional to the gas bag height. Bacteria are supposed to create a pressure increase of typically +20 cm H₂O column. Therefore, a fluid level decrease of 0.6 mm is expected for a gas bag of 3 cm height, assuming a pressure p=1,000 cm H₂O for the gas bag which is approximately equal to the atmospheric pressure.

Gas bag 38 does not have to be made out of elastic material. It is not the gas bag material, but the gas enclosed within it, which acts as an almost ideal "volume spring". This fact allows for an excellent long-time stability of the pressure sensor arrangement according to the present invention. Bacteria can also produce a temporary pressure decrease, however, resulting in an expansion of the gases within gas bag 38. As a result, gas bag 38 should be incompletely filled with gas in order to allow for possible gas volume expansions.

Figure 2:
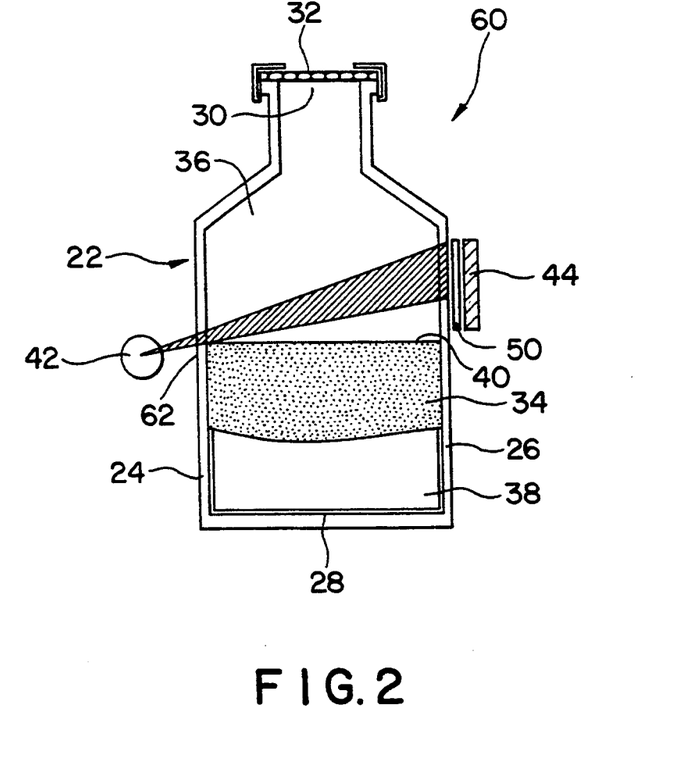
FIG. 2 illustrates an embodiment which takes advantage of optical magnification by imaging the fluid-gas interface near the lamp onto the photodetector.

FIG. 2 illustrates an arrangement that takes advantage of an optical magnification effect. Detection instrument 60 is very similar to instrument 20. It comprises a glass vial 22 with two side walls 24 and 26, a bottom 28, and an opening 30 which is sealed with a septum 32. Vial 22 contains a combined medium/blood mixture 34 with a head space 36. Gas bag 38 is positioned below the upper level 40 of mixture 34. The level detection system comprising light source 42, photodetector 44 and filter 50 may also be the same. The positioning of the light source, photodetector, and filter is different, however. If the distance between light source 42 and the left fluid edge 62 is ten times smaller than the distance from this edge to photodetector 44, than the optical magnification is ×10. This means, a gas bag of 3 cm height creates a 6-mm displacement of the dark/bright transition at the photodetector for a pressure change of 20 cm H₂O column.

Figure 3:
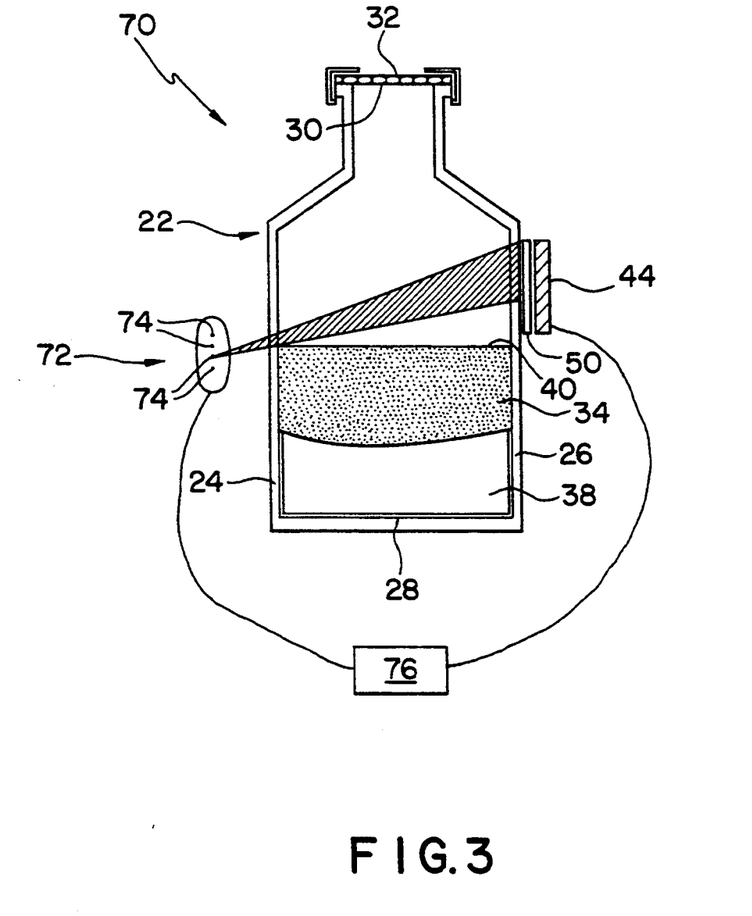
FIG. 3 shows an embodiment similar to that in FIG. 2, but with a multi-filament light source.

FIG. 3 shows an arrangement 70 which is very similar to the one in FIG. 2. It comprises a glass vial 22 with two side walls 24 and 26, a bottom 28, and an opening 30 which is sealed with a septum 32. Vial 22 contains a combined medium/blood mixture 34 with a head space 36. Gas bag 38 is positioned below the upper level 40 of mixture 34. Photodetector 44 and filter 50 may also be the same. The single filament light source 42, however, is replaced with a multi-filament light source 72 in order to adapt the system to varying blood volumes. Light source 72 has horizontally oriented filaments 74 arranged parallel to each other and displaced approximately 1 to 2 mm apart. Light source 72 allows the level monitoring system to be operated for varying amounts of blood inoculated into vial 22. In operation, an instrument control device 76 such as a computer activates the vertical most filament 74 first. This may result in maximum photocurrent output if mixture 34 does not block part of the light. In a next step, control device 76 will turn off the first filament and turn on the next filament down. This procedure is repeated until the photocurrent output signal of photodetector 44 reaches a level equal to approximately 50% of the maximum photocurrent, which is the optimum operating condition for the level monitoring system. For the next reading, control device 76 will start with the previously optimum filament. For a typical vial, such as a BACTEC ® brand vial, 5 ml of blood is recommended. If a possible range of 3 ml to 7 ml is assumed, the fluid level in vials with an inner diameter of 39 mm could vary by 3.4 mm. This means that only a few filaments 74 would be required. Line filament lamps can emit an intense light. The absorption of glass vial 22 in the green/blue spectral range is rather low. Therefore, relatively inexpensive photodetectors such as pn photodiodes can be used in order to attain a sufficient signal-to-noise ratio.

Besides a filament lamp, other suitable light sources are those which have an extremely narrow emitting active area. These include light emitting diode chips and diode lasers. These latter light sources result in very sharp edge imaging and, consequently, high resolution.

Figure 4:
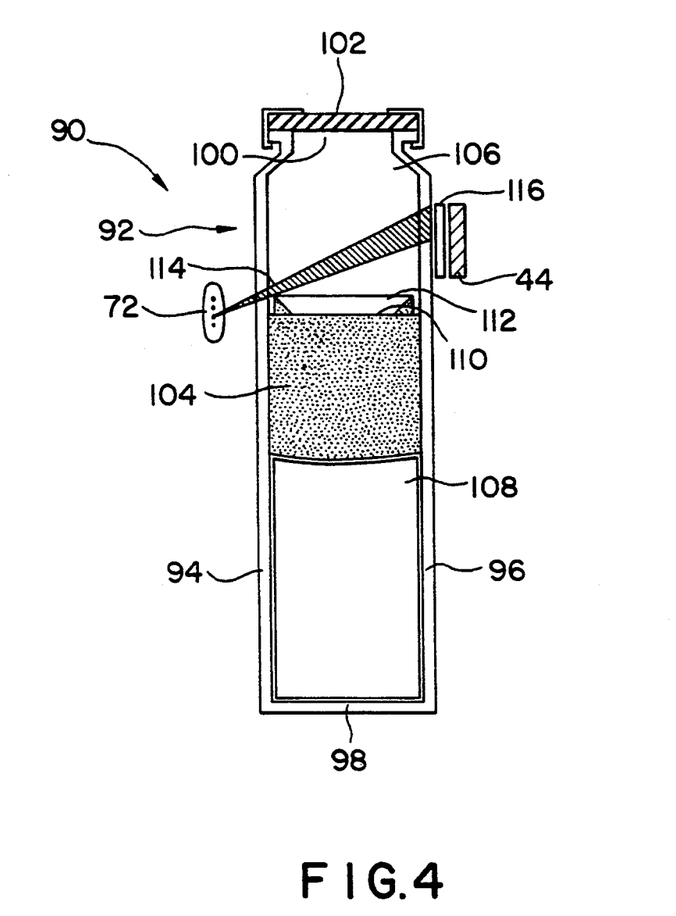
FIG. 4 illustrates an embodiment using an extended gas bag in order to increase the pressure sensitivity, and an opaque float in order to avoid degradation of the pressure resolution by gas bubbles at the fluid-gas interface.

A different embodiment of the present invention, a detection device 90, is shown in FIG. 4. It comprises a glass vial 92 with two side walls 94 and 96, a bottom 98, and an opening 100 which is sealed with a septum 102. Vial 92 contains a combined medium/blood mixture 104 with a head space 106. Gas bag 108 is positioned below the upper level 110 of mixture 104. A multi-filament light source 72 and photodetector 44 are also shown.

Vial 92 has an extended height. As a result, gas bag 108 is larger, resulting in improved pressure change resolution. Assuming a gas bag height of 6 cm, a 12 mm displacement of the dark/bright transition at the photodetector for a pressure change of 20 cm H2O column is obtained. In other words, vials with an extended height offer a chance to reduce the time necessary to detect bacterial growth.

Gas bubbles are known to exist at the fluid-gas interface, particularly when a vial is shaken. Some forms of microorganisms also generate such gas bubbles. In order to circumvent problems connected with such bubbles, detection instrument 90 includes a sharp-edged annular float 112 disposed above upper level 110 of mixture 104. When such a float is used, it is the float edge 114 which is imaged onto photodetector 44. When utilizing a float, no short-pass color filter is necessary. Instead, filter 116 is a narrow-band filter that transmits the light coming from light source 72. Such a filter is advantageous in order to prevent unwanted background radiation from reaching photodetector 44. A narrow-band filter is extremely effective if light source 72 comprises narrow-band light emitting diode chips or diode lasers.

Figure 5:
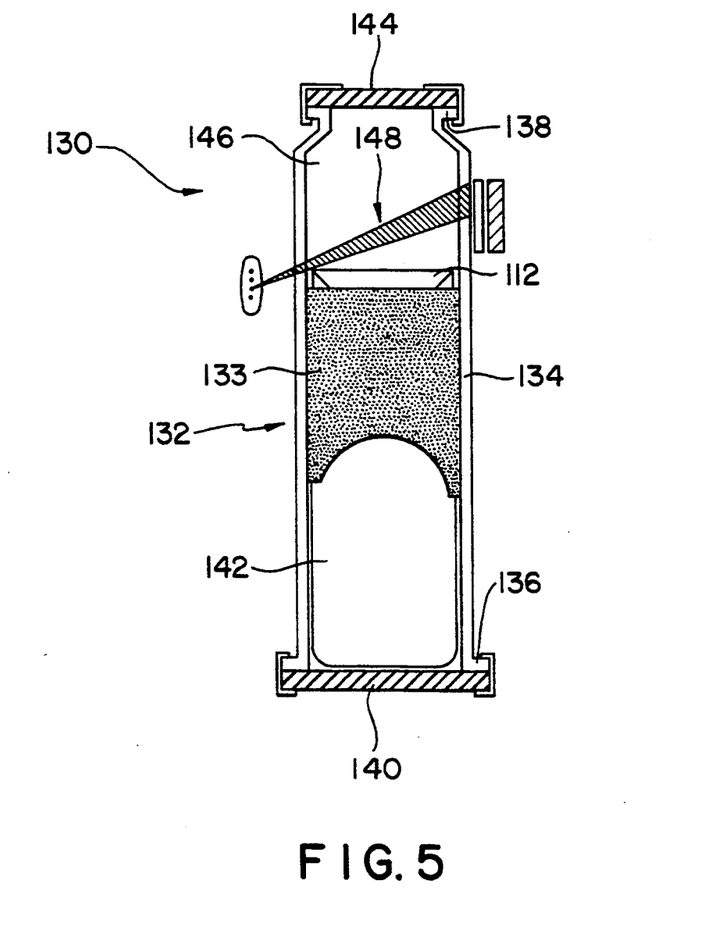
FIG. 5 illustrates an embodiment based on a vial with two flanges with the gas bag secured to the lower flange.

Another embodiment of the present invention is illustrated by the detection instrument 130 of FIG. 5. This arrangement comprises a vial 132 with a medium/blood mixture 133 that is basically a glass tube 134 with two flanges 136 and 138. Lower flange 136 is sealed with a septum 140 which carries a gas bag 142. Gas bag 142 can be attached to septum 140 before sealing vial 132. Septum 144 seals upper flange 138 to create head space 146. This embodiment of the invention is advantageous with respect to ease of blood vial assembly during mass production. The level detection system 148 is identical to that of FIG. 4, as is the use of float 112.

As stated above, any temperature change occurring within the vial head space also generates a pressure change. Obviously, this pressure change is not related to bacterial growth. Therefore, an additional head space temperature measurement would be required in order to distinguish between bacterial growth effects and temperature effects. Non-invasive head space temperature monitoring represents, however, an extremely difficult problem, and has yet to be solved in a practical manner.

In an instrument according to the present invention, however, no head space temperature monitoring is in fact required. Equation (1) can be transformed as follows:

$$p = \frac{mR}{V} T = \rho RT. \quad (4)$$

In (4), $\rho$ is the gas density within the head space. For the temperature-related pressure change, the following may be calculated from equation (4):

$$\frac{dp}{dT} = \rho R. \quad (5)$$

Equation (5) shows that the temperature-related pressure change, dp, does not depend on p or V, but depends only on the gas density. This means that the same temperature-related pressure change is realized for the head space and for the gas bag if the gas densities are equal. Therefore, the upper fluid level in the blood culture vial will not change due to overall temperature changes within the instrument, and no temperature monitoring is required.

In order for this assumption to be most accurate, the gas bag should be in facial contact with the inner periphery of the vial side walls. This way temperature changes affecting the head space will affect the gases within the gas bag to the same extent. Inaccurate results are possible if some of the medium/blood mixture is disposed between the gas bag and the side walls of the vial since the instantaneous temperature may not be the same. In practice, the density of atmospheric air within the gas bag has generally been sufficiently close to the density of gases in the head space so as not to require a special gas mixture for the gas bag. Such a special mixture may be easily prepared, however, and used within the gas bag.

Figure 6:
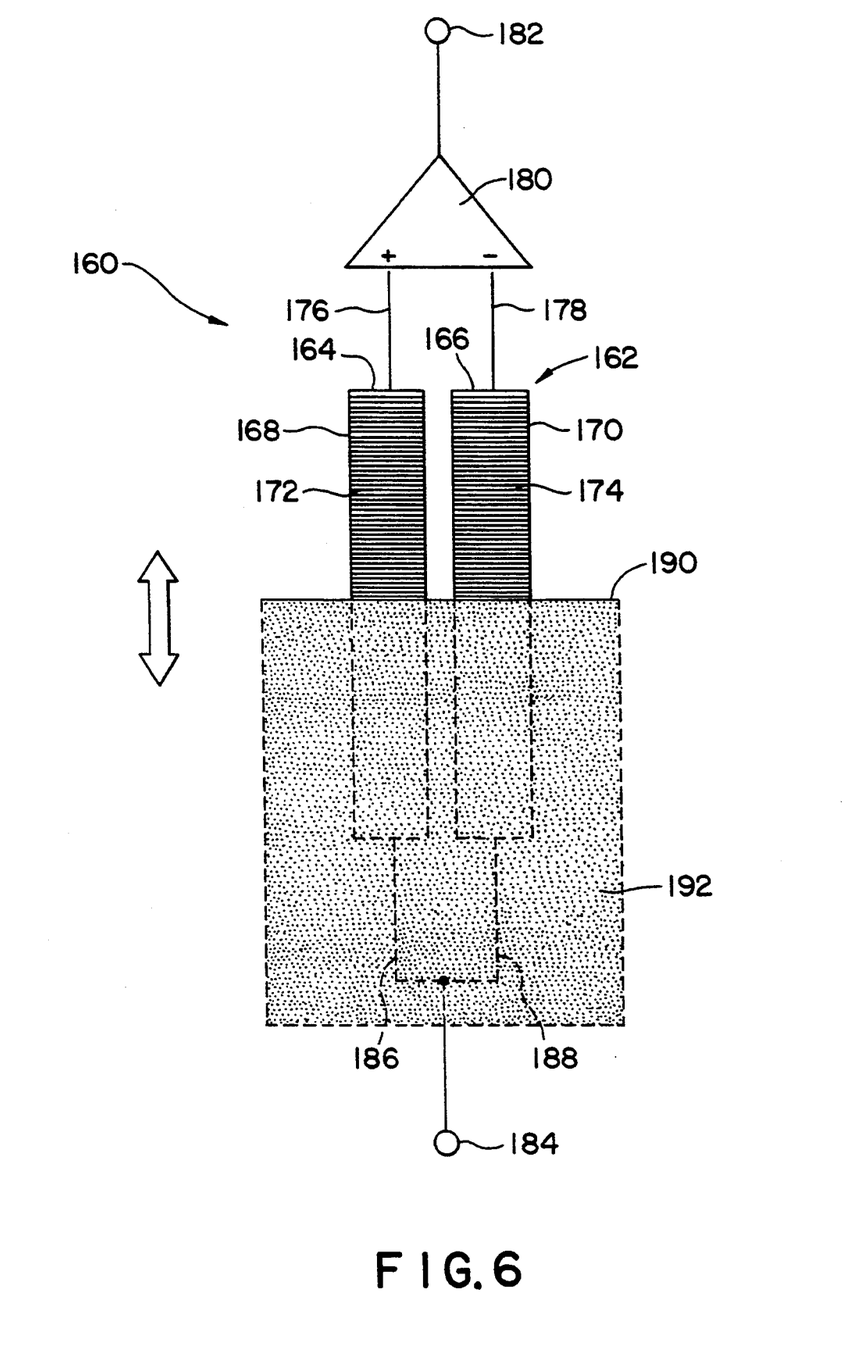
FIG. 6 shows a detector arrangement comprising two large-area photodetectors covered having grating-like transmission masks, and coupled to a differential amplifier.

FIG. 6 shows a photodetector arrangement 160 which may be used in order to make the optical level monitoring system more accurate. Large-area photodetector 162 is split in two vertical segments 164 and 166. Segments 164 and 166 are covered with transmission masks 168 and 170 containing a plurality of uniformly-spaced grating-like horizontal elements 172 and 174. Gratings 172 and 174 are displaced relative to each other by one-half of the grating constant, where the grating constant equals the distance between two adjacent horizontal grating elements. Additionally, masks 168 and 170 have a slightly different overall transmission. The two photodetector outputs 176 and 178 are connected with inputs of a differential amplifier 180 which has an output signal 182. A voltage bias 184 is applied to the photodetector inputs 186 and 188.

If level 190 of medium 192 moves, output signal 182 shows oscillations in accordance with the mask grating constant. Monitoring the output signal oscillations allows for a high pressure resolution. In this way, the linearity of the level monitoring system is determined by masks 168 and 170 and can be made very high. In addition to the oscillating behavior, the output signal shows a trend concerning the output signal DC component. This trend indicates if level 190 is rising or falling, i.e., if the pressure is decreasing or increasing.

The optical transmission of the two grating-like masks 168 and 170 can be approximated by the following equation:

$$T_1(h) = A[1 + R \sin(kh - \theta)] \quad (6)$$

and $$T_2(h) = B[1 + S \sin(kh)] \quad (7)$$

where A and B represent the average transmission, R and S represent the mask transmission modulation, k stands for $2\pi/M$ with M as the grating constant, and h is the fluid level. The mask's relative displacement is characterized by $\theta$, which is set to $\pi$. $\theta$ represents the phase shift between the sensors. By positioning the horizontal grating elements 172 and 174 as discussed above, the phase shift between them is $\pi$ radians or 180°. Thus, the difference between the two photocurrents of each of masks 168 and 170 is maximized for very small fluid level changes.

The fluid level-dependent photocurrent, I(h), is given by the following equation:

$$I_n(h) = \int_0^h J_o T_n(h')dh', \tag{8}$$

where $J_o$ characterizes the system configuration including the light source optical output power, geometry factors, optical filters, and the photodetector responsivity. The subscript n can be either 1 or 2, referring to the two detector segments. The photocurrent difference, $\Delta I$, measured by the differential amplifier is given by the following equation:

$$\Delta I(h) = J_o \left[ (A - B)h - \frac{A R}{k} \cos(kh - \theta) + \frac{B S}{k} \cos(kh) \right]. \tag{9}$$

Figure 7:
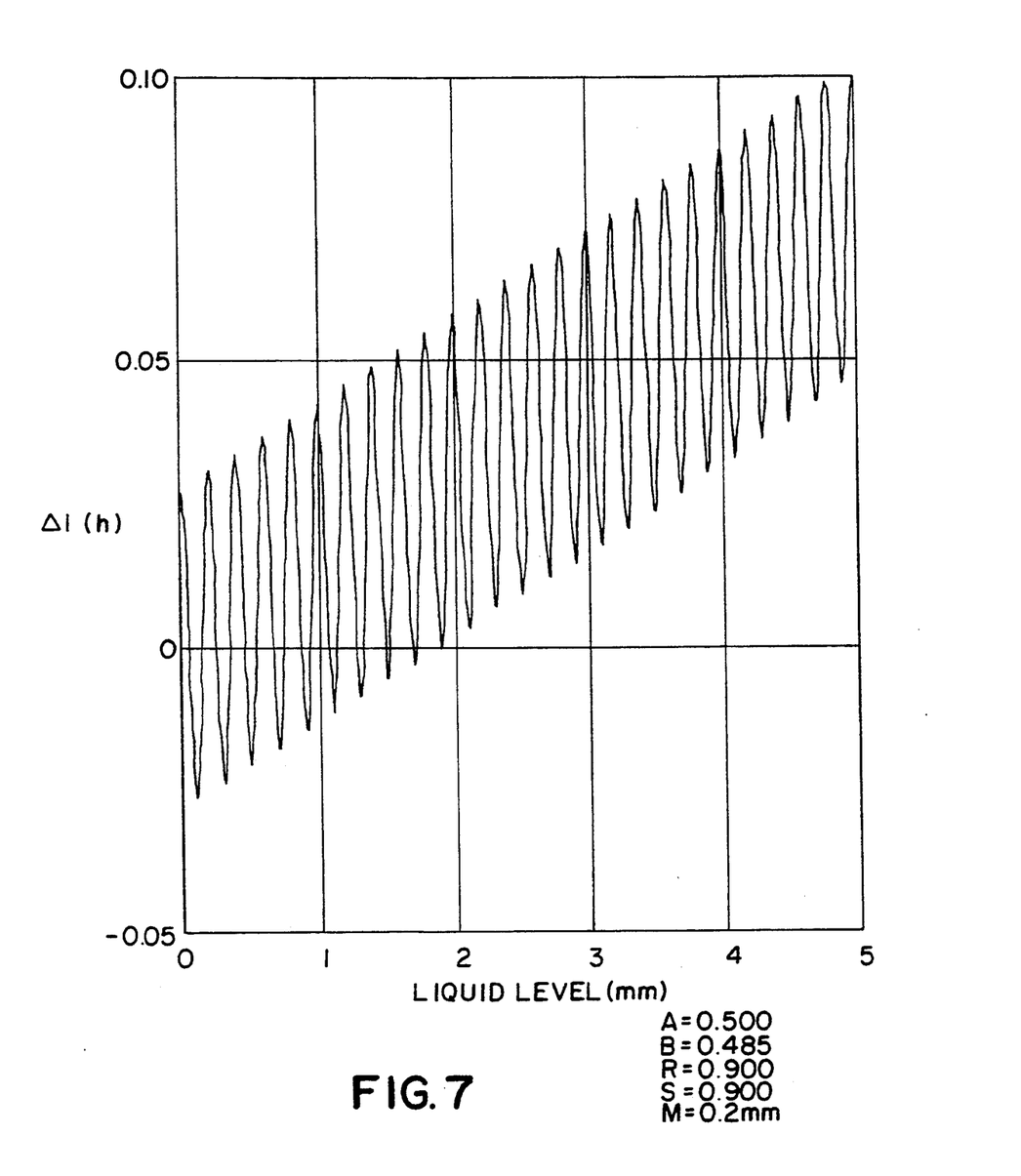
FIG. 7 is a calculated plot showing an oscillating output signal and the fluid level-dependent DC component obtainable using the detector arrangement illustrated in FIG. 6.

FIG. 7 shows the calculated photocurrent difference of equation (9) for specific transmission and modulation values. In the plot shown, the average optical transmission A of mask 168 is 0.500, and mask 170 has an average transmission B of 0.485. Therefore, the masks differ in their transmission by 3%. The transmission modulation R and S for both masks is assumed to be 0.900. The grating constant M is 0.2 mm. FIG. 7 indicates that by introducing masks 168 and 170, fluid level changes less than 0.2 mm can be detected easily. By using computer analysis procedures, high resolutions good linearity and a high dynamic range can be established. The sinusoidal waves create an envelope. From their peaks it is possible to determine how much the fluid level has changed. At the same time, by measuring the average $\Delta I$, the average pressure can be calculated. The average pressure may give information about the type of bacteria. The masks can be mass-produced with the required accuracy and at low cost, using known photographic technologies. It is also possible to use a linear photodetector array instead of a large area analog photodetector.

Figure 8:
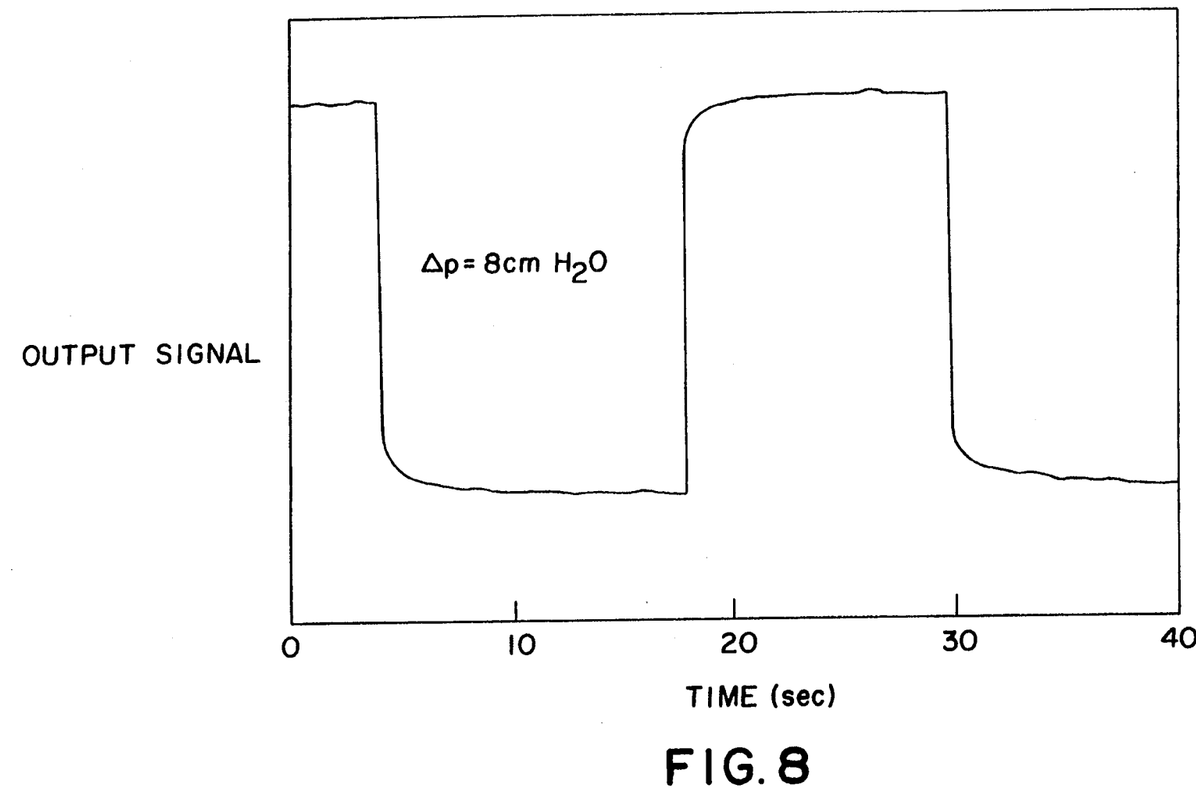
FIG. 8 shows a plot of the output signal obtained using the embodiment of FIG. 2 for periodic pressure changes of 8 cm $H_2O$ column.

FIG. 8 shows a plot of the photodetector output signal with respect to time obtained from a detection instrument 60 according to FIG. 2. Periodic pressure changes of 8 cm $H_2O$ column were introduced.

Figure 9:
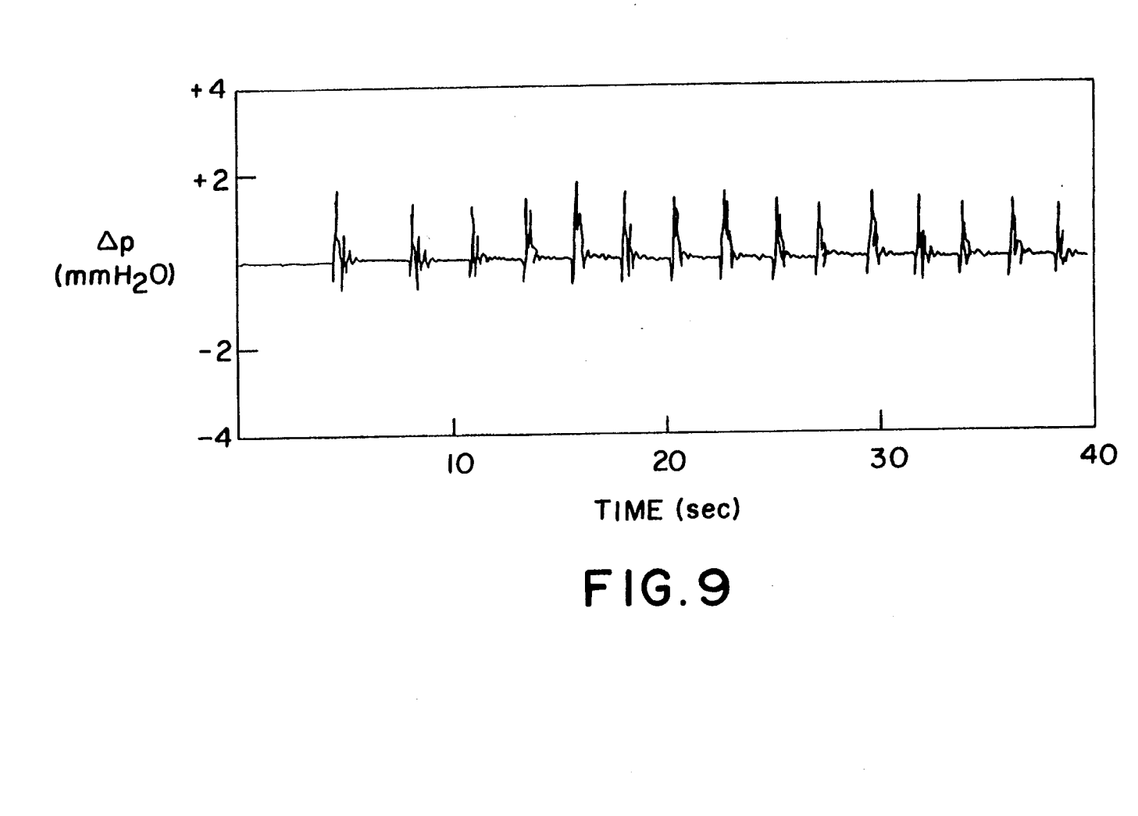
FIG. 9 illustrates the response to strong external mechanical shocks against the vial of a system according to the embodiment of FIG. 2.

FIG. 9 illustrates the response from a detection instrument 60 according to FIG. 2 in terms of a change in pressure change with respect to time. Strong, but brief external mechanical shocks have been imposed upon vial 22.

Figure 10:
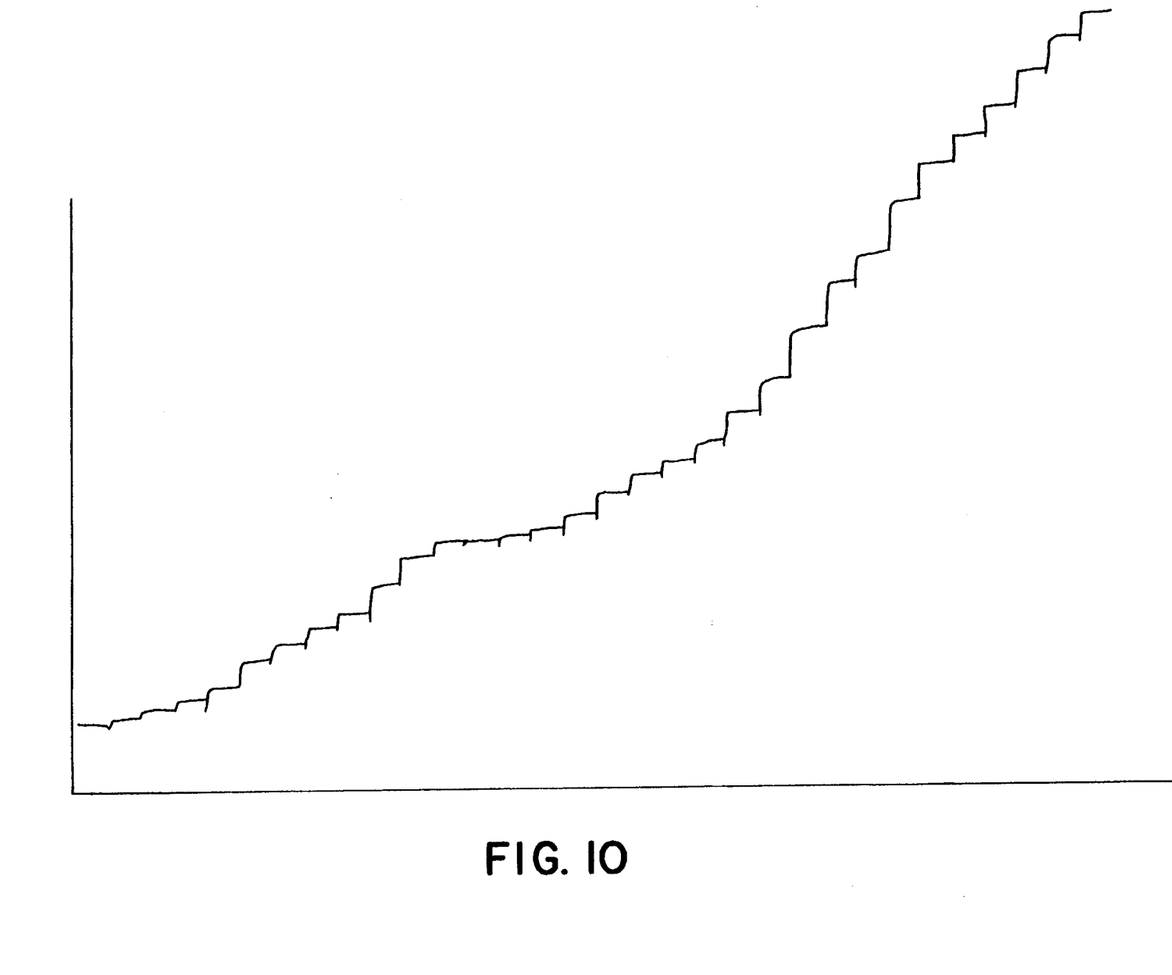
FIG. 10 shows the output signal of an instrument according to FIG. 2 for pressure steps of 1 cm $H_2O$ column within the range $-5$ cm to $+26$ cm relative to room pressure.

FIG. 10 shows the output signal from a detection instrument 60 according to FIG. 2. Pressure steps of 1 cm $H_2O$ column have been introduced within the range of −5 cm to +26 cm relative to atmospheric pressure.

Figure 11:
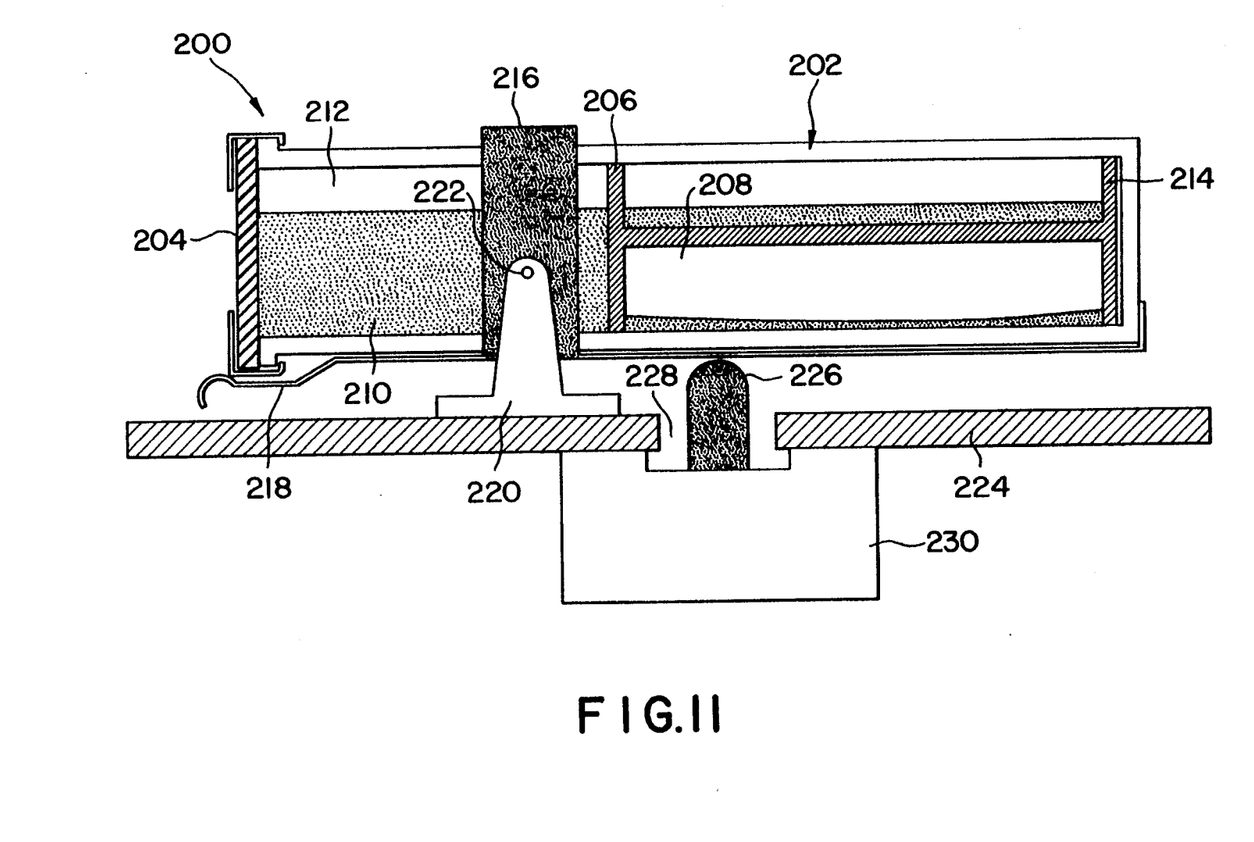
FIG. 11 shows an instrument for detecting biologically active agents according to the present invention, with an embodiment containing a force sensor.

A detection instrument 200 embodying the principles and concepts of the present invention via a different measurement approach is depicted schematically in FIG. 11. The instrument comprises a glass vial 202 sealed with a rubber septum 204 and containing a frame 206 which holds an incompletely inflated gas bag 208. Vial 202 holds a medium/blood mixture 210 which penetrates frame 206 so that gas bag 208 is completely surrounded by fluid. The vial head space 212 extends all the way from the rubber septum 204 to the bottom 214 of vial 202.

Vial 202 is mounted within a sleeve 216 and is kept in position by a plate spring 218. Sleeve 216 is linked to a bearing support 220 via a rocker bearing 222, and the bearing support 220 is mounted onto a base plate 224. The feeler 226 of a force sensor 230 passes though an aperture 228 in base plate 224 and is used to monitor the vial torque.

As shown above in equation (2), the pressure-related volume change, dV, is proportional to the gas bag volume, V. Bacteria are supposed to create a pressure increase of typically +20 cm $H_2O$ column. Therefore, a volume change of 0.72 ml for a gas bag of 36 ml volume is expected, assuming a pressure p=1000 cm $H_2O$ for the gas bag gas, which is approximately equal to the atmospheric pressure. An amount of fluid with a volume dV/2 is moving from one side of vial 202 to the other side to generate a vial torque change. Thus, the fluid level is at least indirectly changed as well.

In order to estimate the expected bacterial growth related torque change, a rod shaped gas bag of length, L, and cross-sectional area, A, extending from the rocker bearing 222 to the bottom 214 of vial 202 are assumed. In addition, it is assumed that the gas bag volume change, dV, results in a constant cross-section change, dA, independent of the distance, l, from rocker bearing 222. Based on these assumptions, the vial torque change, dM, is calculated as follows:

$$dM = \frac{1}{2} \int_0^L \rho g \, dA \, l \, dl = \frac{1}{4} \rho g \, dV L, \tag{10}$$

where $\rho$ is the density of the fluid, and g is the force of gravity, 9.81 m/s$^2$. In equation (10), the factor ½ in front of the integral results from the fact that only half of the moving fluid crosses the rocker bearing.

The force change, dF, measured by force sensor 230 at a distance, l, from rocker bearing 222 is given by the following equation:

$$dF = \frac{dM}{l} = \frac{\rho g \, dV L}{4 \, l} \tag{11}$$

Equation (11) shows, that for L/l=4 the expected force change, dF, is equal to the weight of a fluid with volume dV=0.720 ml. Equation (11) also shows that dF is dependent on L/l, but independent of the absolute value of L. Therefore, an instrument according to the present invention would not necessarily require vials of extended length.

This embodiment also results in the same temperature-related pressure change for the head space 212 and gas bag 208 when the gas densities of each are equal. When the gas densities are the same, no fluid will move across rocker bearing 222 due to overall temperature changes in detector device 200, and no temperature monitoring is required.

A further embodiment of this invention would eliminate the need for a device to measure the torque. Vial 202 may be adjusted with respect to bearing 222 so that an exact equilibrium state is reached. Starting from this equilibrium state, a very fine detuning is accomplished in such a way that the side of the vial not containing the gas bag is lowered until it comes into contact with a base plate. Base plate 224 may be set up so that only a relatively small tilting angle is reached. In this state, a bacterial growth related pressure increase will result in the movement of fluid towards the uplifted vial side. As soon as this side becomes heavier than the originally tipped side, it will tip down instead.

Thus, it is possible to construct an instrument according to the present invention which may be used entirely without electricity.

Thus, while the preferred embodiments of the present invention have been described so as to enable one skilled in the art to practice the apparatus and method of the present invention, it is to be understood that variations and modifications may be employed without departing from the purview and intent of the present invention, as defined in the following claims. Accordingly, the proceeding description is intended to be exemplary and should not be used to limit the scope of the invention. The scope and the invention should be determined only by reference to the following claims.

I claim:

1. An instrument for detecting microorganisms in fluid samples, said instrument comprising:
   a sealable container containing a fluid medium and a gaseous head space above a fluid-gas interface;
   a compressible member submerged in said fluid medium within said sealable container; and
   means for measuring the amount of movement of said fluid-gas interface resulting from microorganism growth related pressure changes within said gaseous head space and compression of said compressible member.

2. An instrument as recited in claim 1, wherein said measuring means is used to determine the change in fluid level.

3. An instrument as recited in claim 1, wherein said compressible member comprises a partially filled gas bag.

4. An instrument as recited in claim 3, wherein said sealable container comprises a glass tube with a lower flange and an upper flange, said lower flange being sealed with a first septum having said gas bag secured thereto and said upper flange being sealed with a second septum.

5. An instrument as recited in claim 1, wherein the density of a gas contained within said compressible member is substantially equal to the density of said gaseous head space.

6. An instrument as recited in claim 2, wherein said measuring means comprises an optical level monitoring system having:
   a light source for directing a light into said gaseous head space in said sealable container; and
   a photodetector with an area for receiving said light from said light source exiting from said gaseous head space, said photodetector generating an output signal representing the amount of movement of said fluid-gas interface based on said received light.

7. An instrument as recited in claim 6, wherein a short-pass color filter is disposed between said light source and said photodetector.

8. An instrument as recited in claim 6, wherein a float is disposed at said fluid-gas interface, with said light source and said photodetector positioned so that said light from said light source intersects a float edge.

9. An instrument as recited in claim 8, wherein a narrow-pass filter is disposed between said light source and said photodetector to prevent unwanted background radiation from reaching said photodetector.

10. An instrument as recited in claim 6, wherein a first distance separates said light source and an edge of said fluid-gas interface, said light intercepting said edge, and a second distance separates said edge from said photodetector, with said first distance being smaller than said second distance.

11. An instrument as recited in claim 6, wherein said light source includes:
    a plurality of horizontally oriented filaments spaced from one another; and
    control device means for selectively activating said filaments until one of said filaments results in said output signal of said photodetector being approximately half a maximum value of said output signal.

12. An instrument as recited in claim 6, wherein said light source is selected from the group consisting of: a filament light element, a narrow-band light emitting diode, and a diode laser.

13. An instrument as recited in claim 6, wherein said photodetector comprises a first segment and a second segment covered by a first transmission mask and a second transmission mask, respectively, each of said transmission masks having a plurality of grating-like elements.

14. An instrument as recited in claim 13, wherein said elements are uniformly spaced, and said elements of said one of said segments are displaced relative to said elements of said other of said structures by one-half of a grating constant.

15. An instrument as recited in claim 14, wherein the optical transmission constant of said mask of said one of said segments is different than an optical transmission constant of said mask of said other of said segments.

16. An instrument for detecting microorganisms in fluid samples, said instrument comprising:
    a sealable container mounted about a pivot point containing a fluid medium and a gaseous head space above a fluid-gas interface;
    a compressible member submerged in said fluid medium within said sealable container on one side of said pivot point; and
    means for measuring the amount of movement of said fluid-gas interface resulting from microorganism growth related pressure changes within said gaseous head space by monitoring a torque of said sealable container.

17. An instrument as recited in claim 16, further comprising a force sensor disposed on said one side of said pivot point, said sensor being used to monitor the torque of said sealable container.

18. A method for detecting pressure changes resulting from the growth of microorganisms in fluid samples, said method comprising the steps of:
    introducing a specimen into a sealable container containing a fluid medium and a gaseous head space above a fluid-gas interface;
    submerging a compressible member in said fluid medium in said sealable container; and
    measuring the amount of movement of said fluid-gas interface resulting from microorganism related pressure changes within said gaseous head space and compression of said compressible member.

19. A method as recited in claim 18, wherein said measuring comprises the steps of:
    emitting light from a light source, said light intercepting an edge of said fluid-gas interface;
    receiving said light at a photodetector; and
    evaluating an output signal produced by said photodetector to determine any movement of said edge of said fluid-gas interface.

20. A method as recited in claim 19, further comprising the step of aiming said light to intercept said edge closest to said light source.

21. A method as recited in claim 20, further comprising the step of placing a short-pass color filter between said light source and said photodetector.

22. A method as recited in claim 19, further comprising the step of placing a float at said fluid-gas interface, with said light source and said and said photodetector positioned so that said light from said light source intersects a float edge.

23. A method as recited in claim 22, further comprising the step of placing a narrow-pass filter between said light source and said photodetector to prevent unwanted background radiation from reaching said photodetector.

24. A method for detecting pressure changes resulting from the growth of microorganisms in fluid samples, said method comprising the steps of:
  mounting a sealable container containing a fluid medium and a gaseous head space above a fluid-gas interface about a pivot point;
  submerging a compressible member in said fluid medium in said sealable container on one side of said pivot point;
  introducing a specimen into said sealable container; and
  monitoring a torque of said sealable container resulting from microorganism related pressure changes within said gaseous head space.

25. A method as recited in claim 24, wherein said monitoring step comprises the steps of:
  placing a force sensor on said one side of said pivot point adjacent said sealable container; and
  evaluating information received from said sensor to determine if said toque of said sealable container has changed.

26. A method as recited in claim 24, wherein said monitoring step comprises the steps of:
  balancing said sealable container about said pivot point; and
  determining when said sealable container has rotated out of equilibrium in response to a change of pressure within said gaseous head space.

27. An instrument for detecting microorganisms in fluid samples, said instrument comprising:
  a sealable container containing a fluid medium and a gaseous head space above a fluid-gas interface;
  a gas bag partially filled with a compressible fluid and submerged in said fluid medium within said sealable container, wherein the density of said compressible fluid within said gas bag is substantially equal to the density of said gaseous head space; and
  means for measuring any change in the position of said fluid-gas interface resulting from microorganism growth related pressure changes within said gaseous head space and compression of said gas bag.

28. An instrument as recited in claim 27, wherein said compressible fluid is a gas.

29. An instrument as recited in claim 27, wherein said measuring means comprises an optical level monitoring system having:
  a light source for directing a light into said gaseous head space in said sealable container;
  a photodetector with an area for receiving said light from said light source exiting from said gaseous head space, said photodetector generating an output signal representing the amount of movement of said fluid-gas interface based on said received light; and
  a filter disposed between said light source and said photodetector.

30. An instrument for detecting microorganisms in fluid samples, said instrument comprising:
  a sealable container containing a fluid medium and a gaseous head space above a fluid-gas interface, said sealable container being mounted about a pivot point;
  a gas bag partially filled with a compressible fluid and submerged in said fluid medium within said sealable container, wherein the density of said compressible fluid within said gas bag is substantially equal to the density of said gaseous head space and said gas bag is disposed on one side of said pivot point; and
  means for monitoring a torque of said sealable container, said torque of said sealable container changing if a portion of said fluid medium moves across said pivot point in response to a change of pressure within said gaseous head space.

* * * * *